United States Patent [19]

Carlson, Jr. et al.

[11] 4,044,119
[45] Aug. 23, 1977

[54] METHOD OF CONTROLLING RELEASE OF MEDICAMENT AND BOLUS THEREFOR

[75] Inventors: Arthur Carlson, Jr., Overland Park; Billy D. Rupe, Leawood, both of Kans.

[73] Assignee: Cutter Laboratories, Inc., Berkeley, Calif.

[21] Appl. No.: 631,885

[22] Filed: Nov. 14, 1975

Related U.S. Application Data

[63] Continuation-in-part of Ser. No. 356,717, May 3, 1973, abandoned.

[51] Int. Cl.$^2$ .................... A61K 9/26; A61K 31/18; A61K 9/64
[52] U.S. Cl. ........................... 424/22; 424/19; 424/36; 424/228; 424/229; 424/359
[58] Field of Search ............... 424/36, 359, 19–22

[56] References Cited

U.S. PATENT DOCUMENTS

| | | | |
|---|---|---|---|
| 629,141 | 7/1899 | Weyland | 424/37 |
| 1,021,674 | 3/1912 | Horowitz | 424/37 |
| 2,406,741 | 9/1946 | Compton et al. | 424/359 X |
| 2,519,487 | 8/1950 | Macek | 424/359 X |
| 2,656,298 | 10/1953 | Loewe | 424/36 X |
| 2,889,248 | 6/1959 | Paterson | 424/359 X |
| 3,275,519 | 9/1966 | Glassman | 424/37 X |
| 3,590,117 | 6/1971 | Christenson et al. | 424/19 |

OTHER PUBLICATIONS

Barber et al. Agriculture 63:111–114 (1956) "Formalin-Treated Skim Milk for Pigs".
Mitchell et al. J. Dairy Res. 27: 103–114 (1960) "Restricted and and Lib. Feeding of Liquid Skim-Milk, with and without the addition of formalin, to fattoning pigs."

*Primary Examiner*—Shep K. Rose
*Attorney, Agent, or Firm*—Schmidt, Johnson, Hovey & Williams

[57] ABSTRACT

An oral dosage medicinal composition for ruminant animals is provided which is processed in a manner to cause a medically effective amount of drug contained therein to be slowly released to the animal by virtue of distribution of the medicament throughout a dry, essentially water-insoluble, slowly digestible matrix. Even slower but therapeutically effective drug release is unexpectedly experienced in feverish animals. A compressed dosage form for oral administration is prepared by first treating an admixture of originally essentially undenatured native milk solids and the drug with a sufficient quantity of an aldehydic agent to insolubilize the milk protein solids. This treated composition is then preferably granulated and the granules compressed under sufficient pressure to form a densified body which is not only resistant to disintegration for over 24 hours when tumbled in water, but also has a specific gravity at least greater than about 1 to cause the dosage form upon administration to a ruminant animal to have a tendency to sink in the rumino-recticular fluids and become entrapped in the rumino-recticular compartments.

37 Claims, 8 Drawing Figures

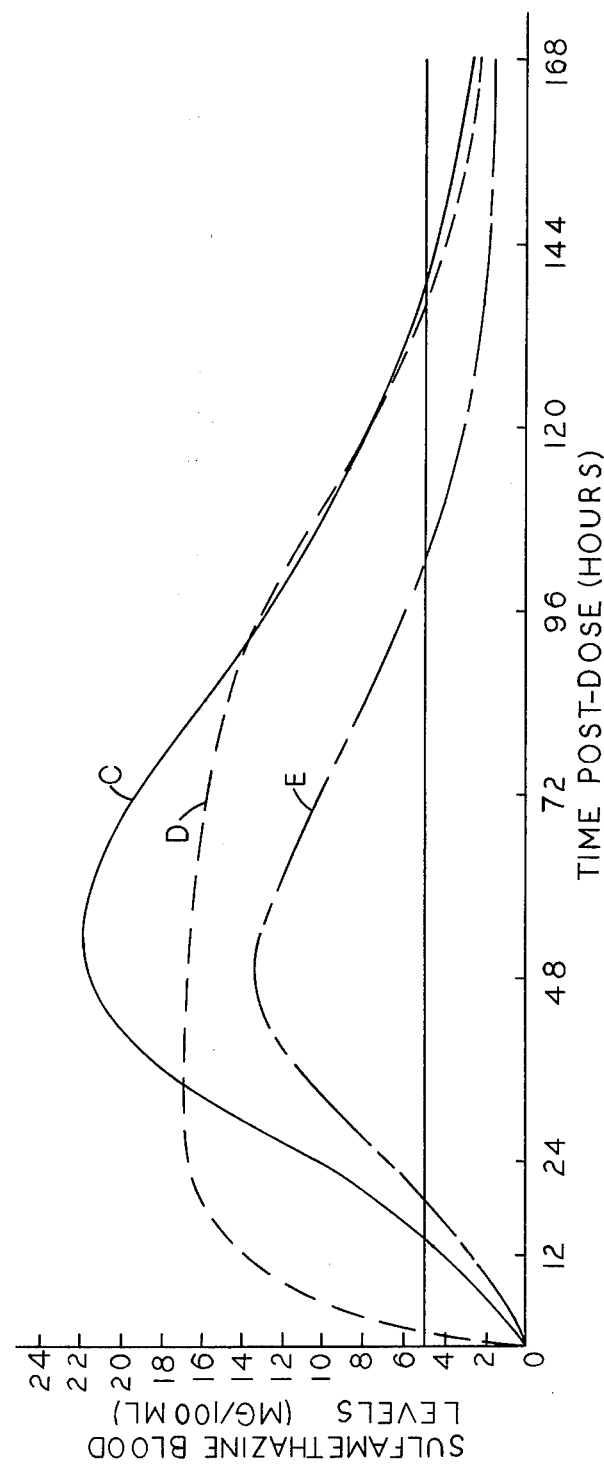

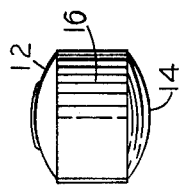
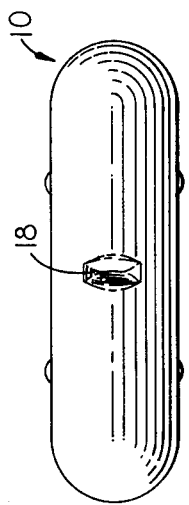
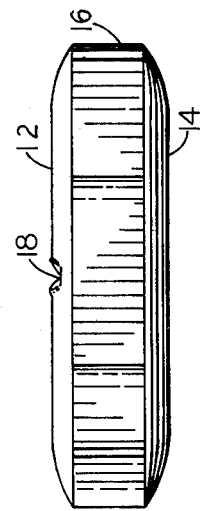
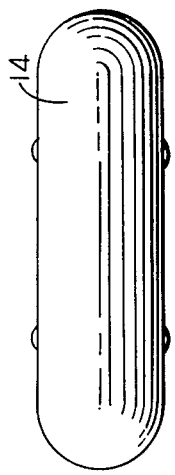
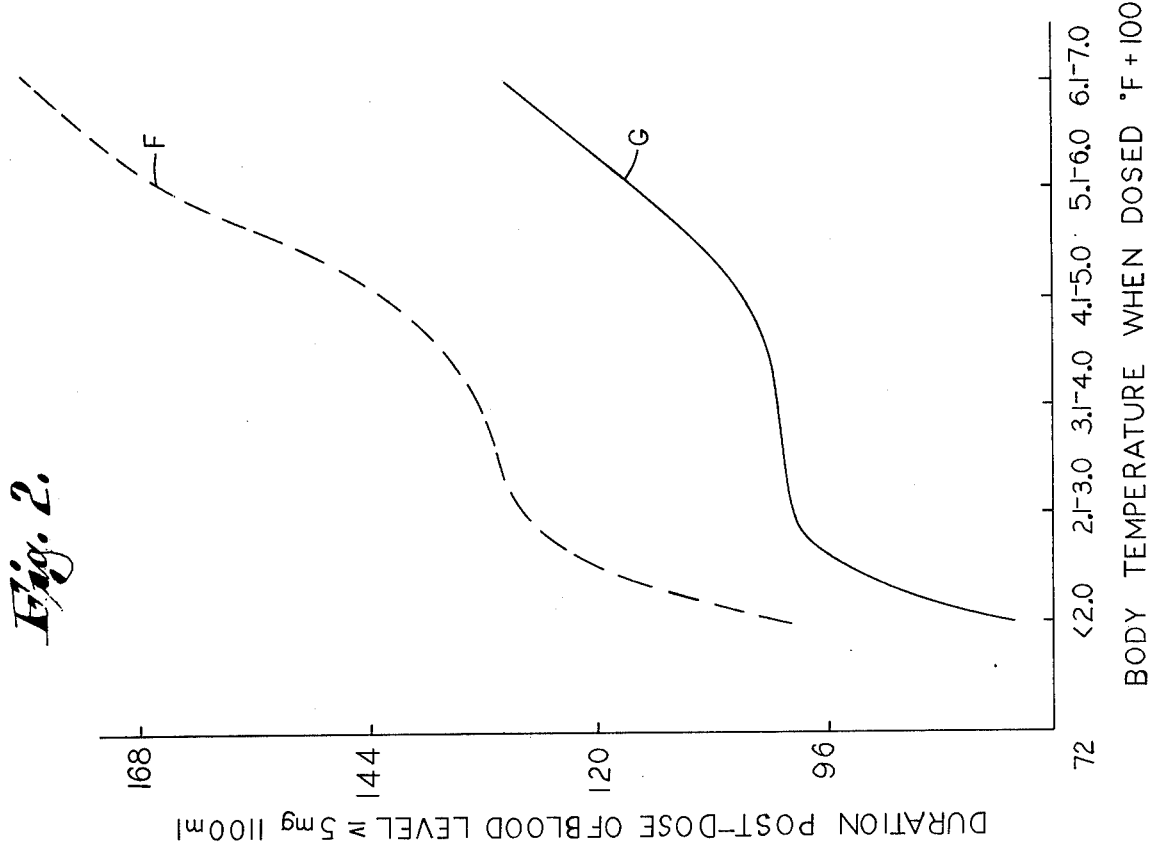

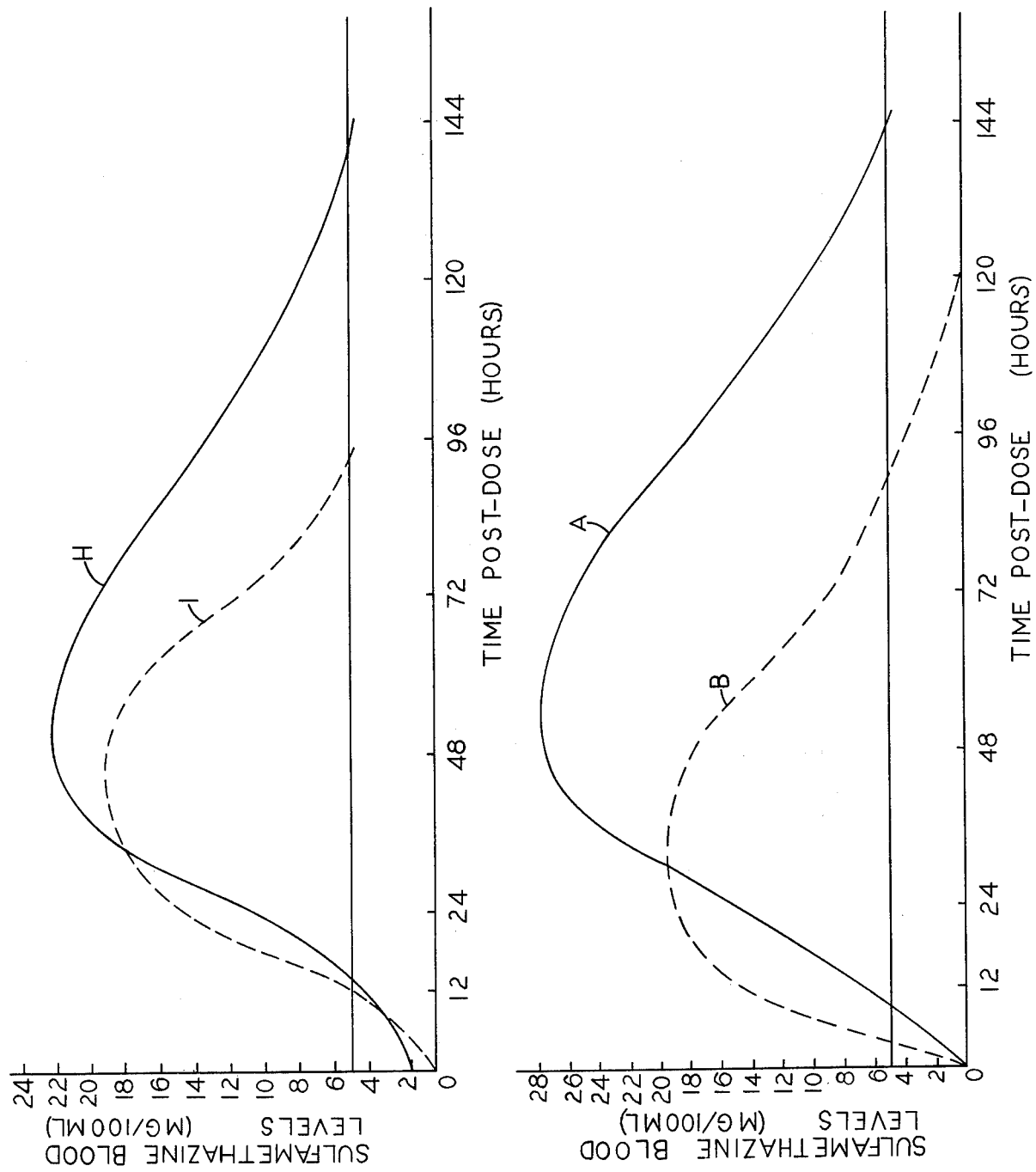

METHOD OF CONTROLLING RELEASE OF MEDICAMENT AND BOLUS THEREFOR

CROSS REFERENCE

This application is a continuation-in-part of application Ser. No. 356,717, filed May 3, 1973, now abandoned, under the same title.

BACKGROUND

This invention relates to a two-component pharmaceutical preparation which is characterized by the property of providing a prolonged release of the medicament component due to gradual and essentially uniform digestion of exposed surfaces of the supporting matrix component. The medicament composition is made up of originally essentially undenatured milk solids which are first reacted with an aldehydic insolubilizing agent in the presence of the drug, granulated, and finally compressed into solid dosage form. More particularly, it is concerned with such preparations and methods of their production which provide extremely efficient prolonged release of drugs in ruminant animals such as cattle and sheep.

In the treatment of illnesses indigenous to ruminants, it is often extremely desirable to provide a medicament composition which has the property of slowly and steadily releasing the drug into the bloodstream of the host. For example, when cattle become ill from diseases such as that commonly referred to as "shipping fever", it is generally necessary to treat them daily with one of the sulfonamide or antibiotic drugs for a period of several days in order to overcome infectious processes, lower their body temperatures and alleviate other debilitating symptoms. In the past this has normally been accomplished by repeated doses of the appropriate drug in order to maintain a therapeutically active amount thereof in the bloodstream of the affected animal. As can be appreciated, this daily procedure increases costs and is a time-consuming procedure, especially when there are a large number of sick animals which must be treated as often as once every 24 hours. Therefore, there is a great need for a method of treatment which allows administration of a dosage form containing a therapeutic drug agent which is of such lasting duration that the necessity for repeatedly administering drug doses to the ruminant animal over an extended period is avoided.

The prolonged release medicament compositions of the prior art can be grouped into four general classes. First, some compositions depend upon retarded dissolution to provide their prolonged release capabilities. An example would be capsules which contain mixtures of beadlets coated with varying numbers or thicknesses of coatings of slowly soluble substances which must be dissolved at varying rates, depending primarily upon the various thicknesses of the coatings.

Another type of prior art composition attempts to produce the desirable prolonged release qualities by coating extremely small granules or whole tablets of medicament with tanned gelatin or collagenic films which are poorly soluble, but slowly digestible or leachable.

Yet another type of prolonged release medicament employs a physical wicking action through pores in a matrix which surrounds the medicinal drug. Examples of this type of prolonged release formulation include those characterized by porous plastic or other insoluble or water repellant carriers whose pores contain and slowly release medicament by an aqueous leaching process.

Finally, a number of formulations have achieved a limited prolonged release capability by attaching medicament molecules to an ion exchange resin so that the medicament will be released when exposed to specific pH environments in certain regions of the gastrointestinal tract.

These prior attempts at producing a satisfactory prolonged release composition have met with only limited success. A primary problem has been the necessity for repeated dosing of the animal because of the relatively rapid release rate of the medicament making them effective for only comparatively short periods of time. More significantly, however, the rate of medicament release from these compositions is heavily dependant upon a generous water content or the presence of relatively specific narrow pH ranges in certain regions of the gastrointestinal tract at certain critical time intervals after treatment of the mammal. Hence, the release patterns can be seriously affected by varying peristaltic activity, pH aberrations or water content in the gastrointestinal tract. Since these factors characteristically vary considerably and cannot be depended upon in sick animals, most of these prolonged release compositions tend to be unpredictable and therefore undesirable in performance. Moreover, these prior art prolonged release dosage forms are characterized by an unpredictability in performance and inefficiency in medicament release, which detracts from their usefulness in practice. In addition, the methods necessary to produce these compositions are often very expensive and difficult to consistently duplicate.

Therefore, there is a decided need in the art for a prolonged release medicament composition which has significantly enhanced prolonged release properties and is also characterized by a uniform and predictable release of the medicament under widely varying conditions of pH and water content in the gastrointestinal tract of the host ruminants. Furthermore, the present invention when used in ruminant animals, has the very unique property of a direct relationship between the degree of fever and duration of the prolonged release period. For example, the higher the fever, the more prolonged the release. Other slow release boluses of the present art designed for use in ruminants do not have this desirable characteristic. In fact, most of them exhibit a shorter release period in feverish animals.

SUMMARY

Accordingly, it has been discovered that the aboveoutlined problems and deficiencies can be overcome by providing a prolonged release composition for the treatment of ruminant animals which comprises a first matrix component of insolubilized originally essentially native milk solids that have been intimately admixed with and support a second drug component which is present in therapeutically significant amounts.

In general, a compressed, self-sustaining dosage form according to the invention is made up of a therapeutically significant amount of a drug intimately entrapped within and uniformly distributed throughout an essentially water-insoluble but slowly digestible matrix made from milk solids which were originally essentially undenatured. As used herein, the phrases "native milk" and "essentially undenatured" refer to milk solids, whether derived from whole, condensed or skim milk in either dry or liquid form.

In practice, the compressed dosage form is produced by first admixing the native milk solids with the drug. Then a predetermined amount of an insolubilizing aldehyde agent such as an aqueous solution of formaldehyde is added that serves to form a cross-linked, lattice-type matrix with the milk protein which renders the milk solids essentially water-insoluble but slowly digestible. The mixture is next granulated, dried and then subjected to sufficient compression to form a relatively dense, self-sustaining oral dosage form. As an alternative to granulation, spray drying of the reacted milk solids and drug may be carried out. It is preferable that the compressed dosage form be capable of resisting significant disintegration when tumbled in water at a temperature of about 37° C. for at least 24 hours.

In the development of the present invention, a number of significant and surprising discoveries were made. One important finding was that only native milk (i.e., essentially undenatured) was operable as the protein matrix. While either whole or nonfat native milk is usable, the constituent proteins extracted therefrom do not yield the desired properties when used as the matrix component. For example, casein or caseinates, which are the chief components of milk, do not serve as an adequate protein matrix when employed alone. Moreover, a recombination of the components of milk (e.g., lactose added to calcium and sodium caseinates) also fails to exhibit the requisite properties. Other unrelated substances such as gelatins, collagen, keratin, soy flour, wheat germ meal, whey, hemoglobin, pinto bean meal, cottonseed meal, soy flour and soybean meal have been tested in the development of the present invention, but all have failed to pass some criteria necessary for the production of satisfactory prolonged release compressed drug compositions. Therefore, it is believed that the specific morphology of native milk is an essential feature which allows the milk to act as a prolonged release matrix after treatment with an appropriate aldehyde insolubilizing agent and compression into a self-sustaining body.

Aldehydic insolubilizing agents for use in the present invention must of course be capable of reacting with native milk to give the necessary degree of chemical modification in the resulting support matrix in order to produce the desired release patterns in the final composition. Further, any excess amounts of insolubilizing agent must be removable from or rendered essentially nontoxic in the final product, and incapable of reacting to any significant degree with the drug component. In preferred forms, aqueous solutions of insolubilizing agents which have an aldehydic functioning group thereon have been found to be especially advantageous. This classification includes solutions of formaldehyde as the preferred agent. However, aqueous solutions of such water-soluble, volatile, aliphatic aldehyde compounds as glutaraldehyde, acetaldehyde, butyraldehyde, propionaldehyde having from 1 to 5 carbon atoms are also useful.

Drugs which have utility in the present invention include, but are not limited to, sulfamethazine, sulfathiazole, sulfadimethoxine and similar sulfonamides. However, other medicaments such as common aspirin, organo-phosphates and the tetracyclines are fullly operable and have excellent prolonged release characteristics.

In the preferred preparation technique, the two phases of the composition (i.e., native milk and drug) are first thoroughly admixed and the aldehyde insolubilizing agent added to effect cross-linking or other chemical modifications of the milk to form a matrix which upon subsequent granulation and drying of the composition entraps and supports the drug in the matrix. The final step involves compression of the granules into a shape which provides an effective drug dosage for administration to sick ruminants. For example, in preparing boluses for administration to cattle, the resultant self-sustaining bodies should preferably resist significant disintegration when tumbled in water at about 37° C. for at least 24 hours. In this way, the bodies retain their integrity in water, but are slowly digestible by proteolytic digestive enzymes or bacterial floral enzymes found in the stomach and gastrointestinal tract of cattle or sheep.

While the physical and chemical actions responsible for the prolonged release effects in such compositions are not wholly understood, it is believed that the digestive enzymes and/or bacterial floral enzymes present in the digestive tract of the host ruminant act to slowly digest the insolubilized milk support matrix, thus releasing the entrapped drug. These enzymes and/or microorganims apparently attack the exposed surface of the tablet or bolus and thus slowly and progressively digest the matrix component; therefore, new surfaces are continually being exposed and the rate at which drug is released can be assumed to be approximately proportional to the total surface area exposed at a given time. Hence, the release rate is initially high and thereafter slowly and steadily decreases over time as the self-sustaining body diminishes in size due to digestion.

DRAWINGS

FIG. 1 is a graphical representation showing comparative prolonged release tests with sick cattle between a single administration of boluses produced according to the present invention as opposed to an equivalent total dosage of a conventional bolus of the prior art, the latter requiring four intermittent administrations spaced 24 hours apart;

FIG. 2 is a graphical representation showing the effect of initial body temperature of sick cattle upon the prolonged release characteristics of boluses made in accordance with the instant invenion;

FIG. 3 is a graphical representation of the comparative prolonged release results obtained from the administration to both sick and healthy cattle of equivalent doses of boluses made according to the invention;

FIG. 4 is a graphical representation of the comparative prolonged release rate results obtained from the administration to two groups of sick cattle of equivalent doses of boluses made according to the invention, one group being given boluses made from water-treated granules, while the other was given boluses made from formaldehyde-treated granules;

FIG. 5 is a side elevational view showing the typical form of a compressed bolus produced according to the invention, in actual size;

FIG. 6 is a front elevational view of the bolus shown in FIG. 5;

FIG. 7 is a rear elevational view of the bolus shown in FIG. 5; and

FIG. 8 is an end elevational view of the bolus shown in FIG. 5.

DETAILED DESCRIPTION

By way of example, a bolus 10, shown for illustrative purposes only as being suitable for administration to sick cattle, preferably comprises a compressed, solid, relatively dense self-sustaining body of the size depicted in FIG. 5-8. Although the precise shape and physical dimensions of the bolus are not critical, it is contemplated that it be sized and configured so that it is usable in universally employed bolus guns familiar to those skilled in the art. Therefore, as shown in those drawings, the bolus 10 includes an arcuate top face 12 and a similarly configured bottom face 14. Connecting the two opposed faces is a substantially vertical, peripherally extending continuous sidewall 16. For convenience, an indentation 18 is fashioned in the approximate center of top face 12 so that thwe bolus can be easily broken into approximate half portions. The bolus illustrated full size in FIGS. 5-8 is especially adapted for administration to cattle. Sheep boluses would be correspondingly smaller.

It is to be understood, however, that other types of compressed oral dosage forms of varying shapes and densities can be produced as desired in accordance with this invention. All that is required is that the dried insolubilized milk and drug composition be compressed to form a self-sustaining body that can be orally administered in conventional manner to the intended ruminant host.

In order to facilitate an understanding of the methods of the present invention, the following Examples detail the critical steps as well as the unique properties of the medicament compositions ultimately produced. It is to be understood, however, that the Examples are for the purposes of illustration only, and are not in any way to be taken as specific limitations upon the overall scope of the invention.

EXAMPLE I

In order to produce boluses especially useful for administration to ruminants, the following processing technique has proved to be useful in production scale runs.

555 kilograms (kg.) U.S.P. grade sulfamethazine is thoroughly mixed in a large ribbon blender with 255 kg. of instant essentially undenatured nonfat dry milk until the two components are initimately and thoroughly admixed. A 1.5% by weight aqueous solution of formaldehyde is then prepared in the ratio of 40.5 cc of 37% by weight formaldehyde solution diluted with tap wter to make a total volume of 1,000 cc. A total of approximately 269 liters of such solution is mixed with the native dried milk and sulfamethazine admixture in a conventional pharmaceutical "pony" blender.

After complete mixing of these ingredients, the resulting product is granulated with an oscillating granulator using a No. 4 mesh screen. These granules are then spread onto large trays and allowed to dry overnight at approximately 140° F.

Following drying, 1 kg. of pharmaceutical grade Carbopol 934P (acrylic acid cross-linked with polyallyl sucrose, sold by the B. F. Goodrich Company) is dissolved in 270 liters slightly warmed 99% aqueous solution of isopropyl alcohol, and the resulting solution is slowly added to the dried granules in a pony mixer. A calcium hydroxide suspension produced by suspending 12 kg. of $Ca(OH)_2$ in 30 liters of isopropyl alcohol is then slowly added to the foregoing while mixing continues until all of the ingredients are thoroughly mixed. The resulting product is again put on trays and allowed to dry overnight at approximtely 140° F. followed by granulation through a No. 5 screen (The Carbopol 934P, calcium hydroxide and isopropyl alcohol do not affect the prolonged released capabilities of the boluses produced by this method. Carbopol 934P is added merely to facilitate compression of the granules and to enhance the appearance and handling characteristics of the final product, while $Ca(OH)_2$ is added to precipitate and hence facilitate drying of Carbopol 934P.)

Following the second drying and granulation steps, the granulated mixture is placed in a large ribbon blender and 135 kg. of U.S.P. grade sulfamethazine and 9 kg. of magnesium stearate are added thereto. This added drug substantially "fills" any interstices remaining in the milk matrix granules, while the stearate serves merely as a conventional lubricant to aid in compression of the self-sustaining bodies.

Standard sized boluses for administration to cattle as depicted in FIGS. 5-8 can be produced, or dosage forms suitable for sheep, for example, can be formed. This is accomplished in a bolus press capable of a compression of approximately 16 tons per square inch. The resulting bolus has a density greater than 1 and preferably about 1.23 grams/cubic centimeter. The chemical composition of each bolus as described in the example is:

| | | |
|---|---|---|
| sulfamethazine | 22.50 | grams |
| nonfat dry milk | 8.50 | grams |
| formaldehyde | trace | |
| Carbopol 934P | 0.06 | grams |
| calcium hydroxide | 0.40 | grams |
| isopropyl alcohol | trace | |
| magnesium stearate | 0.32 | grams |

The following experiments demonstrate the unexpected specificity and criticality of employing native (i.e., essentially undenatured) milk which has been insolubilized with an aldehydic agent as the drug carrier in the prolonged release medicament compositions of the present invention. These formulations exhibit required resistance to disintegration as well as prolonged release properties.

EXAMPLE II a. A quantity of nonfat dried milk was dissolved in water and denatured by steam autoclaving at 121° C. for 45 minutes, then dried at 40° C., ground to a fine powder and used to make boluses as described in Example I (except for omission of the Carbopol 934P). These boluses appeared firm and hard but they disintegrated in 3 minutes when tumbled in tap water at 37° C. (U.S.P. disintegration test). Obviously, with such a short disintegration time, it would not be possible to obtain prolonged release effect; therefore, the autoclaved formulation was not tested in vivo. By contract, boluses made in accordance with Example I (again omitting Carbopol 934P) and thus containing essentially undenatured dried milk reacted with formaldehyde, resisted disintegration for 168 hours.

b. 350 gms. of nonfat dried milk was denatured by boiling with 10 gms. of calcium chloride (the latter was added to facilitate denaturation since it is known to disrupt hydrogen bonding). A granulation including sulfamethazine was made as described in Example I hereof and the granules were digested in 1% papain solution.

c. An identical granulation was made as described in section (a) of this Example, except undenatured milk was used in the formulation, and the granules were digested in 1T papain solution.

The digestion results for the papain tests of pargraphs (b) and (c) are as follows:

TABLE 1

|  | % of Drug Released by Digestion | | |
|---|---|---|---|
|  | 1 Hr. | 3 Hrs. | 5 Hrs. |
| Undenatured Milk [Ex. II(c)] | 3.2% | 26.2% | 27.6% |
| Denatured Milk [Ex.II(b)] | 98.65% | 0.69% | 0.66% |

Small (9/16 inch) tablets were also made from the granulations of the preceding table and disintegration rates (U.S.P. method — tumbled in water) were compared:

TABLE 2

| Undenatured Milk [Ex.II(c)] | 4+ hours |
|---|---|
| Denatured Milk [Ex.II(b)] | 20 minutes |

From the above experiments it is obvious that denatured milk is non-functional in the process of this invention.

EXAMPLE III a. Native condensed whole milk — 384 ml. of commercial essentially undenatured condensed milk was added to 215 gms. of sulfamethazine to produce a slurry of fairly liquid consistency. 4.2 cc. of formaldehyde (0.04287 cc. of 37% aqueous formaldehyde per gm. protein) was added to the slurring and the resulting mixture was dried to a consistency suitable for granulation. The material was then granulated through a No. 4 screen and dried for about 24 hours. Magnesium stearate lubricant was next added and 20 gm. boluses formed therefrom. When tumbled in water at 37° C., the boluses remained substantially intact in excess of six days.

b. In a manner similar to that outlined in section (a) of this Example, a number of othr substances were tested in order to determine their prolonged release capabilities. In each instance a number of threshold criteria were employed to screen those compounds totally unfit for use in a compressed oral dosage form. For example, if a given compound did not produce good discrete granules or if the granules were incapable of forming a self-sustaining body upon compression, they were not subjected to further tests. Table 3 hereunder tabulates the results obtained when the specified matrix substance was first admixed with U.S.P. grade sulfamethazine and a 1.5% aqueous solution of formaldehyde, then granulated, dried, and finally compressed into a solid dosage form (if possible to do so). The compressed forms as applicable were tumbled in water at 37° C. to determine relative disintegration times.

In those instances where the initial criteria were met, water disintegration and optionally in vivo durational effect tests were performed to determine the desirability of a particular compound for use in the present invention (Tables 4 and 5).

In each instance in Tables 4 and 5, 29% of the named compound was used in conjunction with 71% sulfamethazine. The matrix component was treated with an amount of aqueous formaldehyde such that the formaldehyde-protein ratio was about 1:23. The production and experimental protocols used were identical with those outlined in Example I, omitting Carbopol 934P. All percentages are by weight. As can be appreciated from a study of Tables 4 and 5, only the formulas of Experiments Nos. 3, 4, 7, 8, 17, 18 and 19 meet the requirements for use in a compressed oral dosage form.

TABLE 3

| Matrix Material | Gms. | Sulfamethazine (gms) | 1.5% Formaldehyde (cc.) | Test Results |
|---|---|---|---|---|
| Casein | 290 | 710 | 440 | Would not granulate |
| Bovine Serum Albumin | 29 | 71 | 37 | Tablets disintegrated in water in 1 to 4 hours |
| Heat Denatured Bovine Serum Albumin | 29 | 71 | 84 | Tablets disintegrated in five minutes |
| Dried Whole Egg Solids | 29 | 71 | 56 | Tablets disintegrated in five minutes |
| Heat Denatured Dried Whole Solids | 29 | 71 | 55 | Tablets disintegrated in one minute |
| Dry Live Yeast | 29 | 71 | 60 | Tablets disintegrated in less than one hr. |
| Heat Denatured Dry Live Yeast | 29 | 71 | 63 | Tablets disintegrated in about one minute |
| Dried Egg Whites | 29 | 71 | 49 | Tablets disintegrated in 3.5 minutes |
| Heat Denatured Egg Whites | 29 | 71 | 67 | Tablets disintegrated in less than two minutes |
| Pinto Bean Meal | 29 | 71 | 66 | Tablets disintegrated in ten minutes |
| Keratin | 290 | 710 | 600 | Would not compress |
| Soybean Meal | 29 | 71 | 65 | Tablets disintegrated within seconds |
| Defatted Wheat Germ Flour | 29 | 71 | 75 | Tablets disintegrated within seconds |
| Soy Flour Protein | 29 | 71 | 110 | Tablets disintegrated within 30 seconds |

TABLE 4

| Ex. No. | Formula No. | Description | Dissolution Time of Granules in Papain | Disintegration Time of Small Tablet Tumbled in Water at 37° C. | Disintegration Time of Bolus Tumbled in Water at 37° C. | Dissolution Time of Bolus in Ultrasonic Papain Soln. | Onset Time of Therapeutic Blood Level in Cattle | time of Peak Blood Level in Cattle | Duration of Therapeutic Blood Level in Healthy Cattle (Post Adm.) | Duraton of Therapeutic Blood Level in Sick Cattle (Post Adm.) |
|---|---|---|---|---|---|---|---|---|---|---|
| 1 | N.A. 270101 | Sulfamethazine in gelatin capsule Sulfamethazine, |  |  | 20 hrs | 1 hr, min | 2 hrs |  | 84 hrs |  |

TABLE 4-continued

| Ex. No. | Formula No. | Description | Dissolution Time of Granules in Papain | Disintegration Time of Small Tablet Tumbled in Water at 37° C. | Disintegration Time of Bolus Tumbled in Water at 37° C. | Dissolution Time of Bolus in Ultrasonic Papain Soln. | Onset Time of Therapeutic Blood Level in Cattle | time of Peak Blood Level in Cattle | Duration of Therapeutic Blood Level in Healthy Cattle (Post Adm.) | Duraton of Therapeutic Blood Level in Sick Cattle (Post Adm.) |
|---|---|---|---|---|---|---|---|---|---|---|
| 2 | 274080 | Dry Milk, H$_2$O Sulfamethazine, | 1 hr | 28 hrs | | | 6 hrs | 24 hrs | | 88 hrs |
| 3 | 172090 | Dry Milk, H$_2$O, Formaldehyde 1:23 | | | 168 hrs | 2½ hrs | 9 hrs | 48 hrs | | 144 hrs |
| 4 | 277140 | Same as #3 | 5 hrs | 4 hrs | | | | | | |
| 5 | 277140 | Same as #4 but used heat denatured milk | 1 hr | 20 min | | | | | | |
| 6 | 279011 | Same as #5 | | | 3 min | | | | | |
| 7 | 9931-11-B | Same as #3 except added 0.2% Carbopol and Calcium Hydroxide | | | | 2½ 3 hrs | 9 hrs | 24 hrs | 72 hrs | |
| 8 | 9931-06-D | Same as #7 | | | | 2½ hrs | 12 hrs | 48 hrs | 96 hrs | 138 hrs |
| 9 | 031874 | Same as #3, 7 & 8 except hardness reduced from 212.5 to 155 units and mag. stearate from 1% to 0.5% | | | 264 hrs | 3 min | 15 hrs | 48 hrs | 114 hrs | |
| 10 | 272220 37220 178111 | Same as #3 and 4 except substituted gelatin for dried milk | 5 hrs | 1 min | 3 min 7 min | | 1 hr | 24 hrs | 68 hrs | |
| 11 | 372220 | Same as #10 except increased formaldehyde to 1:3.45 | 7 hrs | | 7 min | | 3 hrs | 24 hrs | 66 hrs | |
| 12 | 274220 | Same as #3 except collagen substituted for dry milk and sulfathiazole for sulfamethazine | | 40 min | 2 hrs | | 7 hrs | 7 hrs | 10 hrs | |
| 13 | 172070 | Same as #7 & 8 except casein substituted for dry milk | Would not granulate | | | | | | | |
| 14 | 271110 275180 | Same as #7 & 8 except substituted caseinate for dried milk | | 10 sec 3 min | 13 hrs | | | | | |
| 15 | 273110 274180 | Same as #7 & 8 except calcium caseinate for dried milk | 75 min 42 min | 13 hrs | | | | | | |
| 16 | 377110 271190 | Same as #3 except used Na + Ca caseinates plus lactose in simulate dried milk | | 10 min | | | | | | |

TABLE 5

| Ex. No. | Formula No. | Description | Dissolution Time of Granules in Papain | Disintegration Time of Small Tablet Tumbled in Water at 37° C. | Disintegration Time of Bolus Tumbled in Water at 37° C. | Dissolution Time of Bolus in Ultrasonic Papain Soln. | Onset Time of Therapeutic Blood Level in Sheep | Time of Peak Blood Level in Sheep | Duration of Therapeutic Blood Level in Healthy Sheep (Post Adm.) | Duration of Therapeutic Blood Level in Sick Sheep (Post Adm.) |
|---|---|---|---|---|---|---|---|---|---|---|
| 17 | 179030-P | Same as #7 but contains 1% Carbopol instead of 0.2% | | | | | 11 hrs | 32 hrs | 70 hrs | |
| 18 | 179030 | Same as #3 but not compressed | | | | | 3 hrs | 32 hrs | 63 hrs | |
| 19 | 179030-A | Same as #7 but not compressed and contains 1% Carbopol | | | | | 1 hr | 24 hrs | 57 hrs | |
| 20 | 179030-C | Same as #1 (gelatin capsule) | | | | | 1 hr | 8 hrs | 47 hrs | |

Additional studies were made as recorded in Example IV hereunder to determine if formaldehyde treatment of a mixture containing liquid skim milk and a medicament (i.e., sodium sulfathiazole) would extend the duration of observed plasma levels when compared to an untreated control mixture.

EXAMPLE IV

Eight mixed breed feeder pigs were divided into two groups of four each. Animals in one group were designated as principals while animals in the other group were designated as positive controls. Each group consisted of two males and two females. The average weight of the principals was 120 lbs., while the controls averaged 117 lbs.

All animals were conditioned to the skim milk by removal of their water and feed source each afternoon, with skim milk given the following morning. Feed and water were given after the milk was consumed. One quart (946 ml.) of skim milk/pig/day was fed for two days, followed by 1½ quarts (1,419 ml.)/pig/day for two days and then 2 quarts (1,892 ml.)/ pig/day for two days.

The mixtures administered to each principal consisted of sodium sulfathiazole (N.F., Granular, Merck Lot No. F221990) stirred and dissolved into 2 quarts (1,892 ml.) of skim milk so that it contained 97.2 mg. (1.5 grains) sodium sulfathiazole/lb. body weight. Formalin containing 37% formaldehyde was then added to this mixture to equal 0.5% by volume (9.47 ml./2qt). The mixtures were allowed to stand at room temperature 48 hours before administration.

The mixtures administered to each positive control were prepared in the same manner except the formalin was omitted. These mixtures were also allowed to stand at room temperature for 48 hours.

All solids and liquids were withdrawn from the pigs at 4:00 p.m. one afternoon and replaced after treatment at approximately 6:50 p.m. (principals) and 7:30 p.m. (controls) the following day. Preadministration blood samples were collected and mixed with potassium oxalate, as were samples collected at 1, 3, 5, 7, 12, 18 and 24 hours post-administration.

Blood plasma samples from the pigs were assayed for sulfathiazole by a spectrophotometric adaptation of the Bratton-Marshall reaction with results expressed as mg. % free sulfathiazole. The values listed in Tables 6 and 7 have been corrected for the preadministration levels observed.

Results:

Vomitus was observed from 3 of 4 pigs receiving the formaldehyde-treated mixtures. Volume estimates are included in Table 6. The vomiting occurred with 4 to 11 minutes postadministration. No vomiting was observed in ay of the positive control animals. All animals appeared to be in good health prior to, during and after the study.

The sulfathiazole plasma levels for the two groups (Tables 6 and 7) showed that pigs given the formaldehyde-treated mixture exhibited effective thereapeutic plasma levels (5 mg. %) at none of the sampling intervals, while the positive control group had such levels until the fifth hour post-administration.

TABLE 6

Principal Group
Formula: Sodium Sulfathiazole in 2 quarts (1,892 ml.) skim milk containing formalin (37%) 0.5% by volume. Stored at room temperature for 48 hours before administration.
Dosage: 97.2 ml. (1½ grains) Sodium Sulfathiazole/lb. body weight.

| Pig No. | Time (Hrs Post-Administration) | | | | | | |
|---|---|---|---|---|---|---|---|
| | 1 | 3 | 5 | 7 | 12 | 18 | 24 |
| 43[2] | 1.3[1] | 4.3 | 2.4 | 2.1 | 0.1 | 0.0 | 0.0 |
| 44 | 3.5 | 6.2 | 3.8 | 2.7 | 0.4 | 0.0 | 0.0 |

TABLE 6-continued

Principal Group
Formula: Sodium Sulfathiazole in 2 quarts (1,892 ml.) skim milk containing formalin (37%) 0.5% by volume. Stored at room temperature for 48 hours before administration.
Dosage: 97.2 ml. (1½ grains) Sodium Sulfathiazole/lb. body weight.

| Pig No. | Time (Hrs Post-Administration) | | | | | | |
|---|---|---|---|---|---|---|---|
| | 1 | 3 | 5 | 7 | 12 | 18 | 24 |
| 49[3] | 1.3 | 1.7 | 0.7 | 1.2 | 0.3 | 0.0 | 0.0 |
| 50[4] | 0.3 | 0.7 | 0.7 | 1.4 | 0.2 | 0.2 | 0.0 |
| Average | 1.6 | 3.2 | 1.9 | 1.9 | 0.3 | 0.05 | 0.0 |

[1] Values in mg. % free sulfathiazole in plasma
[2] Vomitus observed - Total approximately 1 cup (236 ml.)
[3] Vomitus observed - Total approximately 4½ cups (1,062 ml.)
[4] Vomitus observed - Total 1+ cup (236+ ml.)

TABLE 7

Control Group
Formula: Sodium Sulfathiazole in 2 quarts (1,892 ml.) skim milk. Stored 48 hours at room temperature before administration.
Dosage: 97.2 mg. (1½ grains) sodium sulfathiazole/lb. body weight.

| Pig No. | Time (Hrs Post-Administration) | | | | | | |
|---|---|---|---|---|---|---|---|
| | 1 | 3 | 5 | 7 | 12 | 18 | 24 |
| 45 | 9.5[1] | 8.9 | 6.8 | 3.6 | 1.5 | 1.1 | 0.1 |
| 46 | 9.5 | 8.4 | 2.7 | 2.4 | 2.0 | 0.3 | 0.0 |
| 47 | 9.6 | 8.0 | 5.5 | 3.0 | 0.5 | 0.0 | 0.0 |
| 48 | 10.0 | 10.2 | 6.4 | 4.7 | 1.6 | 1.0 | 0.0 |
| Average | 9.7 | 8.9 | 5.4 | 3.4 | 1.4 | 0.6 | 0.03 |

[1] Values in mg. % free sulfathiazole in plasma

It is therefore apparant that addition of formaldehyde to a solution of skim milk and sodium sulfathiazole was not functional in providing prolonged effective (above 5 mg. %) blood levels. In fact, it did not provide effective blood levels at any time interval. Vomition is a known side effect of orally administered formaldehyde. But even if one should decide to exclude the three principals that vomited, the one remaining pig only had an effective thereapeutic plasma level at the three hour sampling interval, compared to effective levels at the one, three and five hour intervals for the positive controls.

The desirability of employing an insolubilizing agent in order to render the native milk protein matrix insoluble is further demonstrated by the graphical representation of FIG. 4. Graph A thereof shows the prolonged release capabilities of boluses made in the manner outlined wherein native milk was insolubilized with 1.5% aqueous formaldehyde (except that no Carbopol 934P binder was employed), while Graph B shows the results of an administration of boluses made from non-reacted milk granulated only with water. In each instance an equivalent in bolus form of 22.5 grams of sulfamethazine per 100 pounds body weight was given to four cattle sick with "shipping fever". As can be seen in FIG. 4, aldehydic insolubilization of the granules before granulation and compression materially increases the prolonged release properties of the ultimate product.

In contrast to the substances usable in the present invention as the matrix component, it has been found that a much broader class of insolubilizing aldehyde agents can be used. In general, the only limitations upon the aldehydic insolubilizing agent are that it produce the requisite degree of insolubilization in the native milk protein to render the latter (when sufficiently compressed with a medicament) significantly resistant to disintegration in water, and that it be essentially removable or relatively nontoxic to the host ruminant mammal in use and nonreactive with the medicament employed in the finished dosage form. In particular, it has been found that aqueous solutions of aliphatic, relatively volatile aldehydic insolubilizing agents containing from 1 to 5 carbon atoms are particularly useful in this context. While aqueous formaldehyde is the preferred insolubilizing agent, a number of other aldehydes have been tested and all find utility to a greater or lesser degree. Formaldehyde is especially preferred, however, because it is highly volatile; that is, after the formaldehyde is added to modify the milk protein matrix, any residual amounts can rapidly be substantially entirely removed by evaporation from the granules, thereby preventing any significant toxicity to the host ruminant mammal. For example, in tests run on the boluses produced according to Example I, less than 0.03% by weight of residual formaldehyde was found therein.

The following additional Example establishes that various types of aldehydic insolubilizing agents are functional in insolubilizing native milk protein and impart prolonged release characteristics to the drug compositions prepared therefrom.

EXAMPLE V

Boluses were prepared in accordance with the protocol of Example I except Carbopol 934P was omitted and different aldehydes as identified were substituted for formaldehyde as the milk protein insolubilizing agent. Enzymic dissolution tests were conducted on the granules prior to compression as well as after forming thereof into boluses.

TABLE 9-continued

| SULFAMETHAZINE LEVEL (mg/100 ml whole blood) Formaldehyde-Milk Protein Weight Ratios | | | | | |
|---|---|---|---|---|---|
| Time (Hrs) | o - No Formaldehyde | 1:34.5 | 1:23 | 1:6.9 | 1:2.3 |
| 80 | 2.7 | 1.3 | 6.3 | 3.1 | 6.1 |
| 96 | 1.8 | — | 2.6 | 1.3 | 5.2 |

From the above Table it can be verified that the release rate can be prolonged by increasing the amount of formaldehyde used, and that for the particular insolubilizing agent, a formaldehyde-milk protein ratio of 1:23 gives the best results.

In the use of such aldehydes, it has generally been found necessary to conduct the insolubilizing reaction in the presence of water (as by employing aqueous solutions of the aldehyde in question). This is believed necessary because of two empirically discovered facts. First, when aldehydes are employed in conjunction with anhydrous solvents, good granules cannot be formed. Apparently, it is necessary to have some retained water as water of hydration after drying in order to give the granules the necessary cohesive and elastic properties which facilitate interlocking and binding upon compression.

Additionally, the amount of water present in some manner seems to affect the degree and efficiency of the aldehyde-milk insolubilizing reaction; if too little water is present, insufficient insolubilization occurs, and if an excess is present, the resultant granules can become so hard and dense that they fail to adhere upon compres-

TABLE 8

| Batch No. | Aldehyde Used | Ratio of Aldehyde to Milk Protein | Enzymic Dissolution Test Tumbling of Granules in 1% Papain - % Sulfa Released - Time (hrs.) | | | Ultrasonic Enzymic Dissolution Test Bolus in 10% Papain | Ultrasonic Dissolution Test in Water Without Papain | Bolus Wt(gms) | Bolus Hardness - Enerpac Units | Bolus Thickness (mm.) |
|---|---|---|---|---|---|---|---|---|---|---|
| | | | 1 | 3 | 5 | | | | | |
| 9931-09 | Formaldehyde | 1:23 | 5.5 | 46.0 | 48.0 | 2 hrs 35 min | 31 hrs | 31.50 | 210 | 23.0 |
| 74-102-117 | Acetaldehyde | 1:10 | 55.6 | 42.5 | 1.8 | 1 hr 35 min | — | 31.50 | 260 | 19.8 |
| 74-102-118 | Propionaldehyde | 1:10 | 66.5 | 33.0 | 0.4 | 2 hrs 7 min | — | 30.87 | 240 | 19.2 |
| 74-102-119 | n-Butyraldehyde | 1:10 | 53.7 | 44.0 | 2.3 | 1 hr 43 min | — | 31.31 | 190 | 19.6 |
| 74-102-120 | Glutaraldehyde | 1:10 | 28.4 | 47.3 | 24.3 | 1 hr 35 min | — | 29.14 | 200 | 19.0 |

In view of the foregoing, it is apparent that aqueous solutions of a wide variety of aldehydes are operable to modify the native milk protein matrix in order to provide desirable prolonged release characteristics.

An in vivo blood study was conducted using cattle (2 to 4 cows per group) to determine the effects of varying amounts of formaldehyde (the preferred aldehyde) on a slightly modified standard bolus formula described in Example I (i.e., 71% by weight sulfamethazine, 29% native dried milk, but without Carbopol 934P). The following Table 9 shows the various formaldehyde-milk protein ratios employed and levels of sulfamethazine maintained in the test cattle over time. Each cow was given a bolus equivalent 22.5 grams sulfamethazine per 100 pounds body weight.

TABLE 9

| SULFAMETHAZINE LEVEL (mg/100 ml whole blood) Formaldehyde-Milk Protein Weight Ratios | | | | | |
|---|---|---|---|---|---|
| Time (Hrs) | o - No Formaldehyde | 1:34.5 | 1:23 | 1:6.9 | 1:2.3 |
| 0 | 1.4 | 0.8 | 0.0 | 1.3 | 2.0 |
| 8 | 15.5 | 16.4 | 4.8 | 5.0 | 3.3 |
| 24 | 23.2 | 23.7 | 20.9 | 16.2 | 8.8 |
| 32 | 20.4 | 24.9 | 22.1 | 17.8 | 11.4 |
| 48 | 11.9 | 7.6 | 18.1 | 14.2 | 13.2 |
| 56 | 8.1 | 4.8 | 16.5 | 9.9 | 11.5 |
| 72 | 3.7 | 2.0 | 7.4 | 4.8 | 8.0 | sion. Therefore, in the use of aldehydic insolubilizing agents, optimum amounts of water are necessary. For the broad category of such agents, a water to total dry content ratio of from about 1:2.5 to 1:10 by weight has advantageously been employed. In the most preferred form, this ratio is about 1:3.

It is also desirable in the production of drug formulations according to the invention to minimize as much as possible the total amount of insolubilizing agent employed. For example, if excess amounts of aldehydic insolubilizing agents are used, incompatible side reactions may occur between the agent and the medicament. Therefore, in general the insolubilizing agent should be used in amounts sufficient to give adequate modification of the milk protein matrix while nevertheless minimizing undesirable side reactions. In the case of formaldehyde as shown by Table 9, a formaldehyde to milk-protein ratio of from about 1:50 to 1:2 by weight has been found effective, with a preferred ratio of about 1:23.

EXAMPLE VI

A bolus formulation was made as follows:
| | | |
|---|---|---|
| Sulfamethazine | 2,250 | gms |
| Non-fat dried milk | 1,000 | gms |
| Formaldehyde 1% solution | 771 | cc |

EXAMPLE VI-continued

| | |
|---|---|
| Granulate | |
| Carbopol 934 | 40 gms |
| Isopropyl alcohol | 1,400 cc |
| Calcium hydroxide | 40 gms |
| Isopropyl alcohol | 200 cc. |
| Dry | |
| Compress into 34 gm. boluses | |
| Disintegration time 5 days | |

These boluses were administered to two sheep at a dosage of 22.5 gms. per 100 lbs. body weight and blood levels were maintained above 5 mg. % from the 10th to 86th hour. The formaldehyde-protein ratio in this case was 1:47.4.

Since the aldehyde functional group is the essential insolubilizing factor, slightly different aldehyde-protein ratio ranges are advantageously used when $C_2$ to $C_5$ aldehydes are employed as the protein insolubilization agent in lieu of the preferred formaldehyde reactant agent. Examplary ranges are set forth herein with the best ratios being referenced inside of respective parentheses:

| | |
|---|---|
| 2 carbon atoms - e.g. acetaldehyde | 1:1 to 1:35 (1:10) |
| 3 carbon atoms - e.g. propionaldehyde | 1:1 to 1:25 (1:10) |
| 4 carbon atoms - e.g. n-butyraldehyde | 1:1 to 1:20 (1:10) |
| 5 carbon atoms - e.g. glutaraldehyde | 1:1 to 1:30 (1:10) |

As discussed previously, virtually all medicaments are operable herein, especially if they are in a powdered or fine granular state and do not substantially react with the insolubilizing aldehyde agent during the formulation of the prolonged release compositions. In the use of particular drugs according to the invention, it may sometimes be necessary to modify the production parameters in order to maintain the chemical integrity of the medicament. For example, drying temperatures of about 140° F. have proven successful when sulfamethazine is employed as the medicament. However, other drugs may undergo deleterious reactions at such temperatures and, therefore, the drying step should be performed at lower temperatures or even at low temperatures and under a vacuum. As a consequence freeze-drying or spray-drying processes may be substituted for the granulation and drying steps detailed in Example I. Any such modifications of the processes disclosed herein will be well within the knowledge of one skilled in the art, however.

Exemplary formulations containing different types of drugs are as follows:

EXAMPLE VII

A bolus was made as follows:

| | |
|---|---|
| Sulfadimethoxine | 2,250 gms. |
| Non-fat dry milk | 1,000 gms. |
| Formaldehyde 1% solution | 771 cc. |
| Granulate | |
| Carbopol 934 | 40 gms. |
| Ethyl alcohol 99% | 1,407 cc. |
| Calcium hydroxide | 40 gms. |
| Ethyl alcohol | 1,005 cc. |
| Granulate | |
| Magnesium stearate | 32 gms. |
| Sulfadimethoxine | 450 gms |
| Compress into 34 gm. boluses | |
| Disintegration time 5½ days | |

These boluses were administered to two sheep at a dosage of 22.5 gm. per 100 lb. body weight and effective blood levels above 5 mg. % were maintained from the 10th to 106th hours post administration.

EXAMPLE VIII

A bolus formulation was made as follows:

| | |
|---|---|
| Tetracycline base | 1,000 gms. |
| Non-fat dry milk | 1,000 gms. |
| Formalin | 43 cc. |
| Water | 1,200 cc. |
| Granulate | |
| Magnesium stearate | 18.2 gms. |
| Stearic acid | 36.4 gms. |
| Compress into 30.9 gm. boluses | |
| Disintegration time 3½ days | |

EXAMPLE IX A

A formulation was made according to the following formula, granulated and compressed into oral dosage forms:

| | |
|---|---|
| Coumaphos | 109 gms. |
| Instant non-fat dry milk | 891 gms |
| Formalin | 382 cc |
| Water | 50 cc |
| Granulate dry then add: | |
| Magnesium stearate | 10 gms. |
| Compress | |
| Results: | |

| Tablet Size | Disintegration Time |
|---|---|
| 2 gm. | 9 days |
| 5 gm. | 5 days |

EXAMPLE IX B

A formulation was also made as follows:

| | |
|---|---|
| Coumaphos | 436 gms. |
| Instant non-fat dry milk | 554 gms. |
| Formalin | 237.5 cc. |
| Water | 530 cc. |
| Granulate, dry, then add: | |
| Magnesium stearate | 10 gms. |
| Compress | |
| Results: | |

| Tablet Size | Disintegration Time |
|---|---|
| 30 grains | 8 days |

EXAMPLE IX C

A formulation was made as follows:

| | |
|---|---|
| Coumaphos | 109 gms. |
| Instant non-fat dry milk | 891 gms. |
| Formalin | 382 cc. |
| Water | 500 cc. |
| Granulate, dry, then add: | |
| Magnesium sulfate | 10 gms. |
| Compress | |
| Results: | |

| Tablet Size | Disintegration Time |
|---|---|
| 30 grains | 5 to 6 days |

EXAMPLE X

A tablet formulation was made as follows:

| | |
|---|---|
| Chloramphenicol | 100 gms. |
| Non-fat dry milk | 45 gms. |
| Formaldehyde 1% solution | 35 gms. |
| Granulate | |
| Compress into 7.32 gm. tablets | |
| Disintegration time 2½ days | |

The ratio of drug to milk solids can be varied over a wide range as long as sufficient dried milk is present to form a continuous support matrix for the medicament. For example, the resultant tablet, pellet or bolus can contain from 0.5% to 80% by weight medicament and from 20% to 99.5% by weight native milk. The preferred percentage is from about 40% to 50% drug and from 50% to 60% dried milk.

Compressed compositions made according to this invention are intended to contain medically significant amounts of drugs (as defined by the Federal Food, Drug and Cosmetic Act); however, the percentage composition of the drug will vary depending on relative potencies. For example, atropine is extremely potent in contrast to sulfonamide drugs. Exemplary formulations in this respect are:

EXAMPLE XI A

| 1. | Atropine | 100 gms. |
|---|---|---|
| | Dried milk | 20,000 gms. |
| | Formaldehyde | Trace |
| | Total | 20,100 gms. |

Makes 1,000 boluses weighing 20 gms. each.

EXAMPLE XI B

| 2. | Sulfamethazine | 8,000 gms. |
|---|---|---|
| | Dried milk | 2,000 gms. |
| | Formaldehyde | Trace |
| | Total | 10,000 gms. |

Makes 500 boluses weighing 20 gms. each.

The size of granules employed in the final compression to form tablets or boluses in accordance with the invention can also be varied. In general, the granules must only be of a size which permits their compression into a self-sustaining body. In practice, it has been found that granules of a mesh size from 4 to 50, or preferably from 4 to 14, can advantageously be employed for this purpose.

In order to further establish the effect of particle size on the release pattern, several boluses made according to the formula described in Example I (minus Carbopol) were pulverized to a very fine powder by means of a hammer mill, then recompressed by direct compression into boluses of the same size and hardness as previously.

The original boluses required 5 to 8 days to disintegrate in water while the recompressed boluses disintegrated in 3 days.

From this it can be concluded that although larger particle sizes seem to favor a more prolonged release pattern, nevertheless fairly prolonged disintegration rates can be obtained when the granules are completely destroyed, then recompressed without regranulating.

The compressed dosage forms according to the invention for administration to ruminants are produced under conditions causing the body to have a density of above about 1 gram per cubic centimeter of water, and preferably from 1.1 to 1.6 gm/cc. This prevents the oral dosage form in use from floating upon the surface of the rumen contents or other liquid in the rumenreticulum of the host mammal, and causing it to sink so that the compressed body is not carried out of the rumen too rapidly by the passage of liquids therefrom.

Having described in detail the components, processes and parameters required for the production of prolonged release medicament compositions, the desirable properties of the latter will now be discussed.

When a self-sustaining oral dosage body produced in accordance with the invention is administered to a ruminant, the following process is theorized to occur. Since the dosage form is extremely resistant to disintegration or dissolution in water, the amount of water in the animal's stomach or tract probably has little effect thereon. However, because the dosage form is not immune to digestion by digestive and bacterial floral enzymes, it is likely that the eventual disintegration and dissolution of the bolus can be primarily attributed to breakdown by the proteolytic enzymes present in the digestive tract. Hence, as such enzymes act on the exposed surface of the body by digesting the insolubilized protein matrix, medicament is simultaneously released; this concurrently and progressively exposes new surfaces of the body to be digested in like manner until the entire support matrix is consumed and all of the entrapped drug released. Thus, the release rate appears to be related to the total surface areas exposed at any given time, and it therefore steadily declines as the compressed body erodes and diminishes in size.

The prolonged release capabilities of oral dosage forms produced in accordance with the invention can best be shown with reference to FIG. 1, showing the comparative prolonged release properties of boluses of the present invention compared with a typical fast-release medicament composition of the prior art. The experimental methods used in gathering such data is explained in the following Example.

EXAMPLE XII

Three groups of cattle sick with "shipping fever" were chosen in order to test in vivo the prolonged release capabilities of the present boluses and those of the prior art. The three groups consited of the following:

TABLE 10

| Group | Total Number of Cows | Average Initial Temperature |
|---|---|---|
| C | 143 | 104.00 |
| D | 133 | 104.10 |
| E | 143 | 104.15 |

Group C was orally given an amount of the present prolonged release composition as described in Example I in bolus form equal to approximately 22.5 grams of sulfamethazine per 100 pounds of body weight. This was given at time "0" shown on corresponding Graph C of FIG. 1.

Group D was dosed with a standard rapidly disintegrating sulfamethazine composition being marketed by another pharmaceutical manufacturer, according to the following schedule (total dosage being equal to group C, e.g., 22.5 gms/100 lbs body weight).

TABLE 11

| Time (Hrs) | Dosage |
|---|---|
| 0 | 1½ grains/pound body wt. |
| 24 | ¾ grains/pound body wt. |
| 48 | ¾ grains/pound body wt. |
| 72 | ½ grains/pound body wt. |
| TOTAL | 3½ grains/pound body wt. |

(Three and one-half grains per pound is approximately equal to 22.5 grams per 100 pounds.)

Group E was dosed initially at time "0" with a sulfamethazine bolus in accordance with the invention in an amount equal to approximately 11.25 grams sulfamethazine per 100 pounds body weight. As can be appreciated, this is a "half-dose" of the composition given to C and D.

Turning now to the graphs of FIG. 1, the average prolonged release results obtained for each of the Groups is depicted. This data was collected by intermittently taking blood samples of each animal to determine the sulfamethazine content thereof and averaging all of the results in order to provide the graphs shown in FIG. 1. The average data used to construct the graphs is shown in the following table:

TABLE 12

| Time After Initial Dosage (Hours) | GROUP C<br>Full Dose Prolonged Release (22.5 gms/100 lbs Body Wt.)<br>Mg. Sulfamethazine Per 100 ml. Blood | GROUP D<br>Full Dose Fast Release Sulfamethazine Bolus<br>Mg. Sulfamethazine Per 100 ml. Blood | GROUP E<br>Half Dose Prolonged Release (11.25 gms/100 lbs Body Wt.)<br>Mg. Sulfamethazine Per 100 ml. Blood |
|---|---|---|---|
| 0 | 1.48 | 1.57 | 1.38 |
| 12 | 4.05 | 14.57 | 2.69 |
| 24 | 10.18 | 16.96* | 6.90 |
| 48 | 21.92 | 17.09* | 13.73 |
| 72 | 19.96 | 16.42* | 10.41 |
| 96 | 13.03 | 13.18 | 6.08 |
| 120 | 7.84 | 7.84 | 3.24 |
| 144 | 4.48 | 4.20 | 2.00 |
| 168 | 2.55 | 2.35 | 1.57 |

*Secondary dosages of fast release bolus given at these times in accordance with the above schedule.

A level of 5 milligrams sulfamethazine per 100 milliliters of blood is commonly accepted as a "therapeutically active" level. As shown in the groups of FIG. 1, Graph C (all graphs are denoted with letters corresponding to the groups they represent) shows that at the dosage level defined, the prolonged release composition of the present invention prolongs a therapeutically active amount of sulfamethazine in the cow's bloodstream for a period of almost 140 hours, minus a 14 to 18 hour lag time in onset, while the "half-dose" (Graph E) remains therapeutically active for approximately 105 hours (including the 14 to 18 hours onset lag time). While the fast release standard bolus compositions also maintain a therapeutic level for approximately 135 hours, it is important to note that this can be accomplished only through the use of four successive administrations of the drug over a period of three days. As can be appreciated, these numerous administrations can be a costly and time-consuming procedure, especially if a great number of animals are affected by the disease in question. Moreover, the extra handling and restraint on the animals often causes considerable stress to the latter and can affect their recovery rate. Hence, it is generally much more desirable to provide a therapeutically significant prolonged release of medicament through a single dosing operation. This has been impossible to achieve to any comparable degree with the medicament compositions of the prior art.

During the development of the present invention, it was also unexpectedly discovered that the rate of prolonged release in ruminants is positively affected by the degree of sickness of the animal, as indicated by its initial temperature upon dosing. That is, with a sicker animal having a relatively higher temperature, the compositions of the present invention sustain a therapeutically active amount of drug within its bloodstream for a longer period than would be attainable with an animal less severely ill and showing a relatively lower temperature. This surprising result may be explainable as follows. Because the present compositions are acted on by the enzymes of the bacteris flora present in the ruminant animal's stomach, the rate of dissolution is somewhat dependent upon the concentration of bacteria and protozoa present in the rumen. Additionally, it is known that with increasing body temperature, the bacterial and protozoal population of the ruminant's digestive system is altered so that lesser amounts of them and their associated proteolytic enzymes are present. Therefore, in sicker animals there is a smaller concentration of the required enzymes for digestion of prolonged release compositions, and consequently these formulations remain active for a longer period of time. This property will be more clearly illustrated in the following Example.

EXAMPLE XIII

A number of cattle suffering from "shipping fever" were initially dosed with specified amounts of sulfamethazine boluses produced in accordance with the invention, and their body temperatures were taken. Group F (FIG. 2) was given an amount of bolus equal to approximately 22.5 grams sulfamethazine per 100 pounds body weight, and a second Group G was given a "half-dose" equaling approximately 11.25 grams sulfamethazine per 100 pounds body weight. The total time in which each dosage sustained a therapeutically active amount of sulfamethazine in the blood of each cow was then determined and Graphs F and G of FIG. 2 were prepared from the following data:

TABLE 13

| Initial Temperature Range | GROUP F | | GROUP G | |
|---|---|---|---|---|
| | No. Cows Per Temp. Range | Duration of Therapeutic Level* | No. Cows Per Temp. Range | Duration of Therapeutic Level* |
| 102.0 | 5 | 100 hrs | 3 | 76 hrs |
| 102.1 – 103.0 | 42 | 128 | 38 | 100 |
| 103.1 – 104.0 | 33 | 132 | 32 | 100 |
| 104.1 – 105.0 | 41 | 141 | 37 | 104 |
| 105.1 – 106.0 | 18 | 164 | 26 | 116 |
| 106.1 – 107.0 | 6 | 180 | 6 | 132 |

*Minus a 14 to 18 hour lag time in onset

As shown in the immediately preceding Table and corresponding Graphs F and G, there is a positive correlation between initial body temperature of the sick cow and the amount of time in which a therapeutically active amount of medicament remains in its bloodstream. As the temperature increases from about 102.0° F. to about 107° F. the therapeutically active duration increases from about 100 hours to about 180 hours in the Group given the "full-dose".

Therefore, it is evident that the total prolonged release duration can be estimated from the initial temperature of the animal being dosed. For example, if such an animal has a temperature of from 103.1° – 104.0° F. and a dosage of approximately 22.5 grams sulfamethazine per 100 pounds body weight is administered, the total time in which a therapeutically active amount of sulfamethazine remains in the ruminant animal's bloodstream is approximately 132 hours. Of course, for another given type of animal and disease, other predictive data would need to be consulted in order to determine the approximate duration of medicament release.

It should also be noted that the foregoing release characteristic of the medicament compositions of the present invention in sick animals is extremely surprising in view of the prior art. In the prolonged release compositions heretofore available, there was no way to predict total durational effects or the uniformity of their operation. In fact, in many cases the prolonged release period is shorter in feverish ruminant animals. This is primarily due to the fact that they operate on an entirely different principle than the compositions of the present invention, depending for their operation upon water content or specific pH ranges in certain regions of the gastrointestinal tract of the host ruminant mammal. As shown above, the compositions of the present invention are substantially insoluble in water and are relatively resistant to disintegration at pH 1 to 14. Hence, neither water nor pH variations found in vivo significantly affect their performance.

These effects are further demonstrated by reference to FIG. 3. In that case, a bolus equivalent of 22.5 grams sulfamethazine per 100 pounds body weight was given to two groups, H and I, of cattle. Group H consisted of 143 cows sick and feverish with shipping fever, while Group I consisted of 27 nonfeverish cows. As can be seen from a study of FIG. 3, the identical bolus dosage forms maintained a therapeutically level of sulfamethazine in sick cows for a substantially longer period than in their nonfeverish counterparts.

However, the prolonged release capabilities of the oral dosage forms of this invention are nevertheless substantial (about 90 hours, Graph I, FIG. 4) even in healthy cattle. Therefore, these medicament compositions are also quite useful in treating diseases such as "foot rot" which do not elevate the temperature of the afflicted animal. Moreover, because of this substantial prolonged release in nonfeverish animals, it could sometimes be advantageous to prophylactically administer the oral dosage forms of the invention to healthy animals in order to prevent or lessen the effects of common debilitating diseases.

Having thus described the invention, what is claimed as new and desired to be secured by Letters Patent is:

1. A prolonged release oral dosage drug composition for administration to ruminant animals comprising:
   a solid, compressed dosage form of a size and shape to be orally administered to said ruminant animals and containing a medically effective amount of a drug distributed throughout an essentially water-insoluble disintegration resistant, slowly digestible matrix, said dosage form comprising originally undenatured native milk solids which have been (1) insolubilized in the presence of the drug added thereto by chemical reaction with an effective quantity of an aqueous solution of a substantially water soluble, volatile, aliphatic aldehyde insolubilizing agent having from 1 to 5 carbon atoms, (2) treated to entrap the drug in an essentially dry cross-linked lattice-like matrix of the aldehyde reacted milk protein solids and containing no more than a residual, non-toxic amount of said agent and an insignificant quantity of moisture, and (3) compressed into a self-sustaining body having a density at least greater than 1 to cause the dosage form to sink in the rumino-reticular fluids and become entrapped in the rumino-reticular sacs for slow digestion thereof by proteolytic enzymes upon administration of said dosage form to a ruminant animal,
   said drug being of a type which does not significantly react in a deleterious manner with said aldehydic agent during use thereof to insolubilize the native milk solids and making up about 0.5% to 80% by weight of the compressed dosage form,
   there being about 20% to 99.5% of dried reacted milk solids in said compressed dosage form,
   the ratio of aldehydic insolubilizing agent to milk protein solids and the degree of compression of said reacted milk solids and drug into said dosage form being correlated to provide a densified body which resists total disintegration when tumbled in water at a temperature of about 37° C. for a time period exceeding about 24 hours.

2. A drug composition as set forth in claim 1 wherein said reacted milk solids and drug have been granulated and dried to provide discrete granules entrapping the drug therein prior to compression into said self-sustaining body.

3. A drug composition for administration to ruminant animals as set forth in claim 1 wherein said milk protein insolubilizing agent is a $C_1$ aliphatic aldehyde.

4. A drug composition for administration to ruminant animals as set forth in claim 3 wherein the ratio on a weight to weight basis of the $C_1$ aliphatic aldehyde to milk protein solids during insolubilization thereof is within the range of 1:2 to 1:50.

5. A drug composition for administration to ruminant animals as set forth in claim 3 wherein said $C_1$ aliphatic aldehyde milk protein solids insolubilizing agent is formaldehyde.

6. A drug composition for administration to ruminant animals as set forth in claim 5 wherein the ratio on a weight to weight basis of the formaldehyde to milk protein solids during insolubilization thereof is 1:23.

7. A drug composition for administration to ruminant animals as set forth in claim 1 wherein said milk protein insolubilizing agent is a $C_2$ aliphatic aldehyde.

8. A drug composition for administration to ruminant animals as set forth in claim 7 wherein the ratio on a weight to weight basis of the $C_2$ aliphatic aldehyde to milk protein solids during insolubilization thereof is within the range of 1:1 to 1:35.

9. A drug composition for administration to ruminant animals as set forth in claim 7 wherein said $C_2$ aliphaticc aldehyde milk protein solids insolubilizing agent is acetaldehyde.

10. A drug composition for administration to ruminant animals as set forth in claim 9 wherein the ratio on a weight to weight basis of the acetaldehyde to milk protein solids during insolubilization thereof is 1:10.

11. A drug composition for administration to ruminant animals as set forth in claim 1 wherein said milk protein insolubilizing agent is a $C_3$ aliphatic aldehyde.

12. A drug composition for administration to ruminant animals as set forth in claim 11 wherein the ratio on a weight to weight basis of the $C_3$ aliphatic aldehyde to milk protein solids during insolubilization thereof is within the range of 1:1 to 1:25.

13. A drug composition for administration to ruminant animals as set forth in claim 11 wherein said $C_3$ aliphatic aldehyde milk protein solids insolubilizing agent is propionaldehyde.

14. A drug composition for administration to ruminant animals as set forth in claim 13 wherein the ratio on a weight to weight basis of the propionaldehyde to milk protein solids during insolubilization thereof is 1:10.

15. A drug composition for administration to ruminant animals as set forth in claim 1 wherein said milk protein insolubilizing agent is a $C_4$ aliphatic aldehyde.

16. A drug composition for administration to ruminant animals as set forth in claim 15 wherein the ratio on a weight to weight basis of the $C_4$ aliphaticc aldehyde to milk protein solids during insolubilization thereof is within the range of 1:1 to 1:20.

17. A drug composition for administration to ruminant animals as set forth in claim 15 wherein said $C_4$ aliphatic aldehyde milk protein solids insolubilizing agent is n-butyraldehyde.

18. A drug composition for administration to ruminant animals as set forth in claim 17 wherein the ratio on a weight to weight basis of the butyraldehyde to milk protein solids during insolubilization thereof is 1:10.

19. A drug composition for administration to ruminant animals as set forth in claim 1 wherein said milk protein insolubilizing agent is a $C_5$ aliphatic aldehyde.

20. A drug composition for administration to ruminant animals as set forth in claim 19 wherein the ratio on a weight to weight basis of the $C_5$ aliphatic aldehyde to milk protein solids during insolubilization thereof is within the range of 1:1 to 1:30.

21. A drug composition for administration to ruminant animals as set forth in claim 19 wherein said $C_5$ aliphatic aldehyde milk protein solids insolubilizing agent is glutaraldehyde.

22. A drug composition for administration to ruminant animals as set forth in claim 21 wherein the ratio on a weight to weight basis of the glutaraldehyde to milk protein solids during insolubilization thereof is 1:10.

23. A drug composition for administration to ruminant animals as set forth in claim 2 wherein said granules have been sized to mesh size of from about 4 to 50 before being compressed into said dosage form.

24. A drug composition for administration to ruminant animals as set forth in claim 1 wherein is provided on a weight basis about 40% to 50% of said drug and 50% to 60% of dried milk.

25. A drug composition for administration to ruminant animals as set forth in claim 1 wherein the ratio of water to total dry contents initially present during insolubilization of said milk protein solids is from about 1:2.5 to 1:10 by weight.

26. A drug composition for administration to ruminant animals as set forth in claim 1 wherein said dried reacted milk solids and drug are compressed to a density within the range of about 1.1 to 1.6.

27. A drug composition for administration to ruminant animals as set forth in claim 1 wherein said dried reacted milk solids and drug are compressed to a density of about 1.23.

28. A drug composition for administration to ruminant animals as set forth in claim 1 wherein said drug is sulfamethazine.

29. A drug composition for administration to ruminant animals as set forth in claim 1 whrein said drug is sulfathiazole.

30. A drug composition for administration to ruminant animals as set forth in claim 1 wherein said drug is sulfadimethoxine.

31. A drug composition for administration to ruminant animals as set forth in claim 1 wherein said drug is a tetracycline compound.

32. A drug composition for administration to ruminant animals as set forth in claim 1 wherein said drug is an organophosphate.

33. A drug composition for administration to ruminant animals as set forth in claim 32 wherein said organo-phosphate is coumaphos.

34. A drug composition as set forth in claim 1 wherein said dried reacted milk solids and drug are compressed into a bolus dosage form sized for balling gun administration to cattle.

35. A drug composition as set forth in claim 1 wherein said dried reacted milk solids and drug are compressed into a bolus dosage form sized for balling gun administration to sheep.

36. A method of orally treating feverish ruminant animals with a prolonged release thereapeutic drug composition comprising:
   administering to an afflicted ruminant animal a solid, compressed dosage form containing a medically effective amount of an anti-bacterial drug distributed throughout an essentially water insoluble, disintegration resistant slowly digestible matrix,
   said dosage form consisting essentially of originally undenatured native milk solids which have been (1) insolubilized in the presence of the drug added thereto by chemical reaction with an effective quantity of an aqueous solution of a substantially water soluble, volatile, aliphatic aldehyde insolubilizing agent having from 1 to 5 carbon atoms, (2) treated to entrap the drug in an essentially dry cross-linked lattice-like matrix of the aldehyde reacted milk protein solids and containing no more than a residual, non-toxic amount of said agent and an insignificant quantity of moisture, and (3) compressed into a self-sustaining body having a density at least greater than 1 to cause the dosage form to sink in the ruminoreticular fluids and become entrapped in the ruminoreticular sacs for slow digestion thereof by proteolytic enzymes upon administration of said dosage form to said feverish ruminant animal,
   the ratio of aldehydic insolubilizing agent to milk protein solids and the degree of compression of said granules into said dosage form being correlated to provide a densified body which resists total disintegration when tumbled in water at a temperature of about 37° C. for a time period exceeding 24 hours,
   said anti-bacterial drug being of a type which does not significantly react in a deleterious manner with said aldehydic agent during use thereof to insolubilize the native milk solids and making up about 0.5% to 80% by weight of the compressed dosage form,
   there being about 20% to 99.5% of reacted milk solids in said compressed dosage form with the ultimate drug release rate in the feverish ruminant animal being slower with higher body temperatures.

37. A method as set forth in claim 36 wherein said anti-bacterial drug administered to the feverish ruminant animal is sulfamethazine.

* * * * *